United States Patent [19]
Tombs

[11] Patent Number: 5,176,805
[45] Date of Patent: Jan. 5, 1993

[54] REVERSE-POLARITY GEL ELECTROPHORESIS

[75] Inventor: Michael P. Tombs, Bedford, England

[73] Assignee: Hoefer Scientific Instruments, San Francisco, Calif.

[21] Appl. No.: 6,553

[22] PCT Filed: Jul. 17, 1986

[86] PCT No.: PCT/GB86/00416
§ 371 Date: Dec. 16, 1986
§ 102(e) Date: Dec. 16, 1986

[87] PCT Pub. No.: WO87/00635
PCT Pub. Date: Jan. 29, 1987

[30] Foreign Application Priority Data

Jul. 17, 1985 [GB] United Kingdom ............... 8518030
Jan. 28, 1986 [GB] United Kingdom ............... 8602089

[51] Int. Cl.⁵ .................... G01N 27/26; B01D 57/02
[52] U.S. Cl. ....................... 204/182.8; 204/299 R
[58] Field of Search .......... 204/182.8, 182.9, DIG. 9, 204/299 R, DIG. 8, 182.1

[56] References Cited

U.S. PATENT DOCUMENTS 3,506,554 4/1970 Broome ................. 204/182.8 X

FOREIGN PATENT DOCUMENTS

1046370 5/1953 Fed. Rep. of Germany.

Primary Examiner—John Niebling
Assistant Examiner—John S. Starsiak, Jr.
Attorney, Agent, or Firm—Limbach & Limbach

[57] ABSTRACT

Improved resolution of proteins and other macro molecules in gel electrophoresis is obtained by causing the molecules to move through the gel under the influence of an electrical potential, the polarity of which is intermittently reversed. While the current is reversed for a brief period, any molecules that have become trapped in pores in the gel have an opportunity to escape. For proteins, the frequency of current reversal should be from 1 to 5,000 reversals per second and the influence of the reverse current should not be greater than 50% of the forward or driving current. Current reversal can be used in combination with multiple transverse electrical fields.

2 Claims, 5 Drawing Sheets

REVERSE-POLARITY GEL ELECTROPHORESIS

The present invention relates to methods of separating mixtures of charged macromolecules (which term includes charged molecular complexes) by electrophoresis.

In gel electrophoresis, for example in polyacrylamide gels, a primary objective is high resolution and for this reason the migrating zones need to be kept as sharp as possible. Zone spreading is due in part to diffusion, but we have found that particularly for large molecules in concentrated gels, another broadening effect can occur. This is because the migrating molecules enter pores in the gel from which they cannot escape except by the way in which they entered. The effect is that of a 'lobster pot' entrapment. With the much larger nucleic acid molecules similar interactions lead to loss of discrimination between different sizes of molecules. The effect of a smooth direct current is to drive the molecules deeper into the trap.

The practical effect is that a sample placed at the origin is not carried forward completely, but a "trail" of entrapped material is left behind as the sample migrates through the gel, leading to diminution of the migrating zone of material. If the initial sample is small, the entrapped material can eventually comprise such a large percentage of the total material initially placed at the origin, that the quantity of material in the migrating zone becomes too small to be observable or analysable. With much more sensitive detection methods now being available, it is now practical and desirable to apply much smaller samples to the gel and hence the foregoing problem has assumed much greater significance.

Recently, it has become important to be able to separate very large molecules such as chromosomal-size DNA. Some measure of success has been achieved by the use of complex arrangements of multiple electrodes to apply to the gel electrical fields in intermittently variable transverse (orthogonal) directions, which in practice is difficult to put into effect especially where multiple samples are being analysed simultaneously on the same gel. Such a system has been described by Cantor et al in U.S. Pat. No. 4,473,452, and in *Cell*, 37 (1984) pages 67 to 75. Their system involves the use of multiple arrays of diode-controlled electrodes, to achieve the desired complex field effects without encountering problems due to short-circuiting between the different arrays of electrodes.

The present invention provides an electrophoretic method of separating charged macromolecules, in which method the macromolecules are induced to move through a gel or similar physically-impeding medium, in a predetermined direction away from an origin, under the influence of an electrical potential the polarity of which is intermittently reversed.

In one embodiment of the invention, the current reversal is parallel to the predetermined direction in which the macromolecules are induced to move.

By this surprisingly simply technique, which in its simplest embodiment can be achieved by the use of a single pair of electrodes in standard electrophoresis equipment, and with a conventional power source supplemented by an appropriate switching device, it is possible to achieve molecular separations at least as effectively as by the more complex electrode arrangements hitherto proposed (e.g. by Cantor et al), and indeed in some instances superior separations may be achieved. Hence in its simplest form, the benefits of the invention can be obtained using conventional electrophoresis equipment supplemented by a switching means capable of providing the necessary unbalanced current reversal.

In the separation of DNA, the importance and practical benefits of current reversal have very recently been independently verified by Olson et al, and was the subject of a lecture delivered by Olson in Heidelberg in November 1985. Furthermore, a disclosure by Cantor et al in *Nature*, 319 (1986) pages 701 to 702, suggests that in their multiple field approach, field shapes leading to angles between alternate fields that range from 100° to 150°, enhance resolution and inherently this also amounts to recognition, that a reversal of direction is important.

In a further embodiment of the invention, a primary current applied in the predetermined direction is supplemented by a second applied electrical potential having a component at right angles to the predetermined direction, and the polarity of the second applied electrical potential is intermittently reversed. The primary current can be applied constantly, intermittently and also reversed if desired.

In a yet further embodiment of the invention, a plurality of electrical potentials are applied to the gel, each potential having a component at right angles to the predetermined direction and a component parallel to the predetermined direction, the relative magnitudes and relative constancies or frequencies of the potentials being such that the molecules experience a net influence in the predetermined direction.

Despite the intermittent current reversal, the macromolecules must still experience a net potential influence in a particular direction, averaged over a period of time. The "forward" influence must therefore exceed the "reverse" influence. In practice, the influence of the reversed current preferably should not be greater than about 50% of the "forward" influence.

The use of current reversal requires a higher current for the same rate of migration. In a typical example, 40 mamp at 400 volts may be needed from the power source, with the current reversed for 1/6 of the time. The comparable constant DC requirement would be 27 mamp. Despite the greater electrical current, problems due to coulombic heating are unlikely to be encountered. Present-day electrophoretic equipment already includes adequate temperature control arrangements.

The frequency of reversal should be such as to allow ample time for Brownian motion diffusion of the molecules to avoid the trap. This will depend on the size and natural diffusion rates of the molecules involved. By way of example, for proteins a frequency of 25/second is very suitable, but between 1 and 5000 reversals per second can be effective. For larger molecules, such as DNA fragments, less frequent reversals may be more appropriate, with intervals of 1 minute or more being suitable for exceptionally large molecules.

The voltage and current employed can be typical of those used in gel electrophoresis, generally ranging from 5 mamp to 50 mamp and 100 to 500 volts measured at the output from the power source. Times required for the electrophoretic separation are again typical and vary from 2 to 18 hours, more usually between 2 and 8 hours, depending on the precise conditions and the substances to be analysed. For exceptionally large molecules, higher currents and voltages, and longer separation times, may be advantageous.

The method of the invention can therefore be performed using any electrophoresis equipment in which all or part of the normal DC power source has been replaced by or supplemented by a variable reversible power source. In one embodiment, the time ratio of the reversible current can be varied, giving a longer forward pulse and a relatively shorter reverse pulse, at constant voltage.

Performance of the invention requires a power unit comprising a power source and an associated (preferably integral) switching means having the capability to reverse the polarity of the output current, to vary the frequency of such reversal, and preferably also to vary the "mark time" (i.e. to be able to vary the ratio between the duration of the forward and reverse currents). Preferably, the power source should be capable of providing a smooth DC output of at least 1,000 volts, to cater for the needs of present-day electrophoretic procedures. The provision of multiple outputs is also advantageous, enabling a sequence of current formats to be applied successively to one or more sets of electrodes, or enabling several electrophoresis units to be operated from the same power unit.

Figure 2:
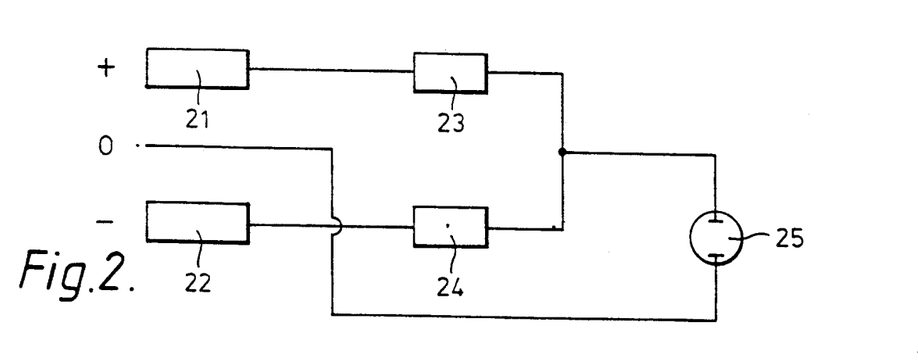
FIG. 2 illustrates a switching system using two separate power supplies switched to an electrophoresis cell via two switching means.
Figure 3:
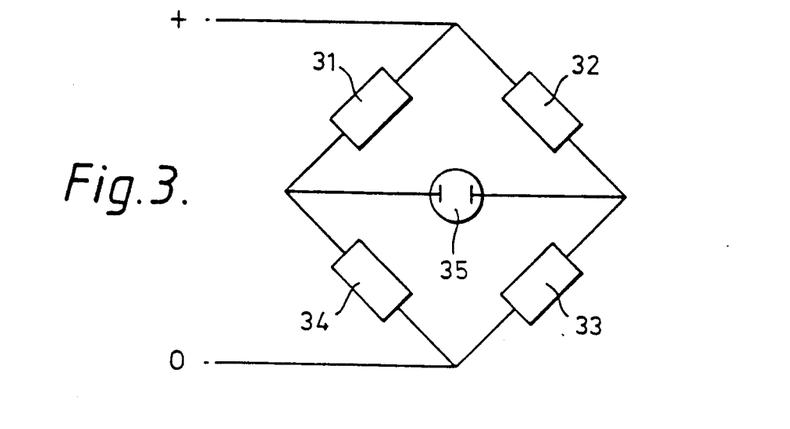
FIG. 3 illustrates still another switching arrangement, with a bridge circuit which requires only a single power supply.

The essential techniques by which to construct a power unit having the capabilities mentioned above are standard in the electronics art, and the detailed construction of the power unit does not form part of the invention. It is well within the skill of one versed in the electronics art to manufacture a suitable unit having been appraised of the technical functions that the power unit must provide. By way of example only, a suitable switching waveform can be generated manually (for long time intervals between reversals of the current), or by the use of analogue or digital timers, or by microprocessors. The waveform can be used to drive relays which switch the high-voltage supply, or which drive metal oxide semi-conductor switches (MOS) or bipolar transistors which can handle high voltages. The use of multiple MOS in series, by-passed by high impedance resistors, is already common practice and enables very high voltage currents to be switched repeatedly and rapidly. Examples of suitable switching arrangements are depicted in FIGS. 1 to 3 of the accompanying drawings, and are described briefly below.

BRIEF DESCRIPTION OF THE DRAWINGS

FIG. 1b illustrates a higher-voltage wave form which is the output of the power driver and which is the inverse of the input voltage illustrated in FIG. 1a.

Figure 1:
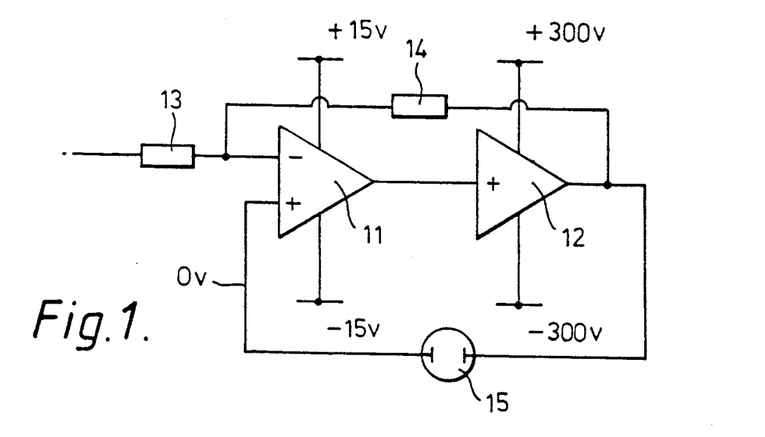
FIG. 1 illustrates a switching unit utilizing an operational amplifier connected to a power driver.
Figure 1A:
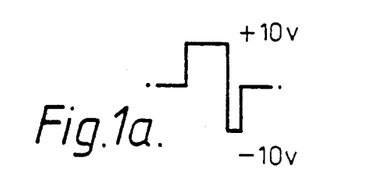
FIG. 1a illustrates a low voltage wave form which serves as the imput to the operational amplifier of FIG. 1.
Figure 1B:
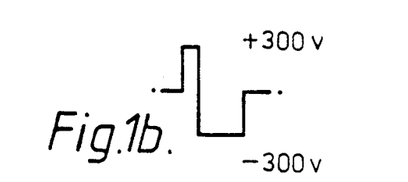

FIG. 1 illustrates a switching unit utilising an operational amplifier 11 linked to a power driver 12. A low voltage waveform (illustrated in FIG. 1a), is fed via a first resistor 13 of value $R_1$, into the operational amplifier 11. The power driver 12 and the operational amplifier 11 are connected by a feed-back loop via a second resistor 14 of substantially higher value $R_2$. The electrophoresis cell 15 is connected to the output of the power driver 12 and to the "zero" or "ground" potential terminal of the operational amplifier. The initial waveform (FIG. 1a) can be generated for example using a microprocessor. The output voltage V from the power driver is determined by the relationship $$V = -\frac{R_2}{R_1}$$

and hence the output waveform will be at a very much higher voltage and will be the inverse of the input voltage. This is represented by FIG. 1B. The various voltages, such as the low-voltage (±15 volts) and high-voltage (±300 volts) supplies, in FIGS. 1, 1a and 1b are given purely by way of example to illustrate the principle.

FIG. 2 illustrates a switching system using two separate power supplies 21 and 22 (positive and negative), switched via switching means 23 and 24 respectively to an electrophoresis cell 25. In this embodiment the switching means could be relays, bipolar transistors or metal oxide semi-conductor switches.

FIG. 3 illustrates a bridge circuit which has the advantage that only a single power supply is needed. The bridge is of conventional design and comprises four switching units 31, 32, 33 and 34 with an electrophoresis cell 35 in the centre of the bridge. As in any electrical bridge circuit, current reversal in this instance can be achieved by alternatively switching on and off the switch pairs 31 plus 33 and 32 plus 34. Here, the switching units can also be relays, bipolar transistors or MOS.

An electrophoresis apparatus for use in accordance with the invention will comprise essentially a gel supporting unit ("cassette"), a solvent tank in which the cassette can be placed, appropriate electrodes and electrical connectors therefor, and an appropriately switched power unit as described above. It will be appreciated that in the simplest embodiment, all of these components are standard items of electrophoresis equipment except for the modified power supply. Accordingly, the benefits of the invention can be attained without the need for elaborate electrodes and special gel supporting units.

In other embodiments of the invention, combinations of reversible and constant currents can be used to separate large fragments of DNA, for example. There are many possible combinations, but Examples 3, 4 and 5 illustrate three of them that are effective. Two types of current reversal are used together with Examples 4 and 5, while in Example 3 a boustrophedon reversal had the advantage that diagonal migration was avoided. In these embodiments of the invention a switching unit not normally part of an electrophoresis apparatus was used, with additional electrodes at the side of the gel. Current reversal in accordance with the invention can therefore be advantageously applied, if desired, in combination with transverse field electrophoresis techniques such as those described by Cantor et al.

The invention is particularly useful in effecting the separation of complex mixtures of biological materials, such as proteins and nucleic acids.

The invention is illustrated by the following Examples.

EXAMPLE 1

This example illustrates the way in which the use of current reversal reduces zone spreading. 15 g of acrylamide, 0.75 g of methylene-bis-acrylamide, 0.2 ml of tetramethyl diaminomethane were dissolved in 100 ml of trisglycine buffer (1.2 g Tris hydroxy amino methane and 5.76 g glycine/liter). Gelation was induced by adding 0.5 ml ammonium persulphate solution (10% w/v) and two identical gels of $140 \times 160 \times 0.75$ mm cast in a conventional vertical slab electrophoresis apparatus. Each was loaded with between 0.1 $\mu$l and 8 $\mu$l of a solution of bovine serum albumin to give a range of loads of from 0.05 up to 5 $\mu$g or 10 $\mu$g of protein. One gel was then run at 10 mamp for 7 hours with a smooth DC supply, and the other with 15 mamp for 7 hours with the frequency of current reversal set at 25/sec, and the reversed current running for 1/6 of the time. This reversible current was produced using a switching circuit as depicted in FIG. 3 and described in principle earlier. A unipolar power supply was fed to 4 bipolar transistors arranged in a bridge, and the mark time controlled by a conventional variable transistor oscillator. The distance migrated in both gels was closely similar. Several repeat runs were performed.

Protein was detected by silver staining and the area of the zone measured by using a Quantimet image analyser. Average results, depicted graphically in FIG. 4, showed that the area of the zone was less when current reversal was used.

Figure 4:
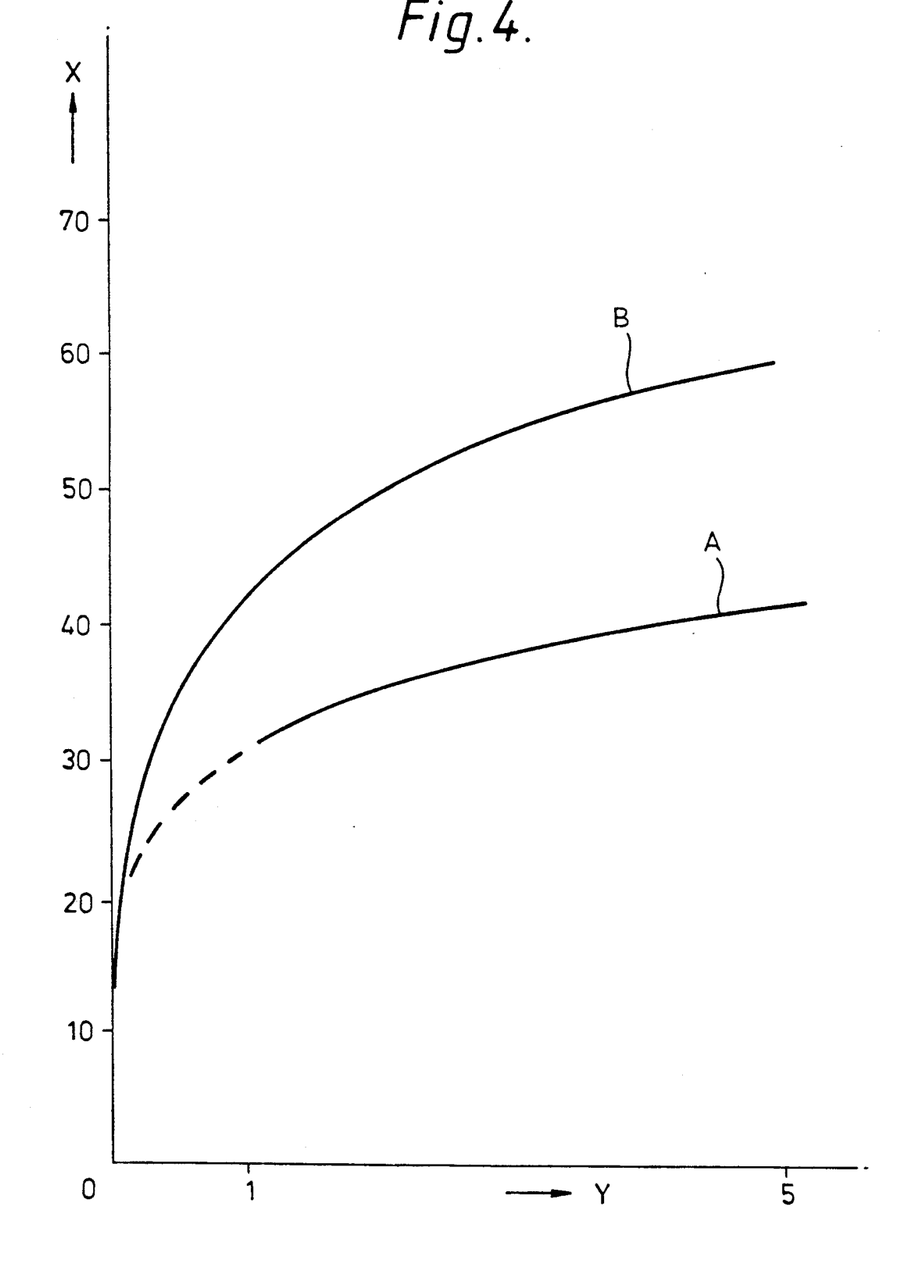
FIG. 4 graphically represents the area of the strained migrated zone versus the initial load placed at the origin. Line A shows the typical relationship when current reversal is employed, line B showing the typical control using constant DC power.

In FIG. 4, X represents the area of the stained migrated zone, in mm$^2$, and Y represents the initial load placed at the origin, in $\mu$g. Line A shows the typical relationship when current reversal is employed, line B showing the typical control result using constant DC power. The way in which the zone spreads sideways—that is to say at right angles to the direction of migration—can be used to estimate the area of the zone if diffusion alone was responsible for spreading. These areas were estimated and showed that using current reversal reduced the area to that expected as a result of diffusion alone. Current reversal would not be expected to affect diffusion-driven zone spreading.

Figure 5A:
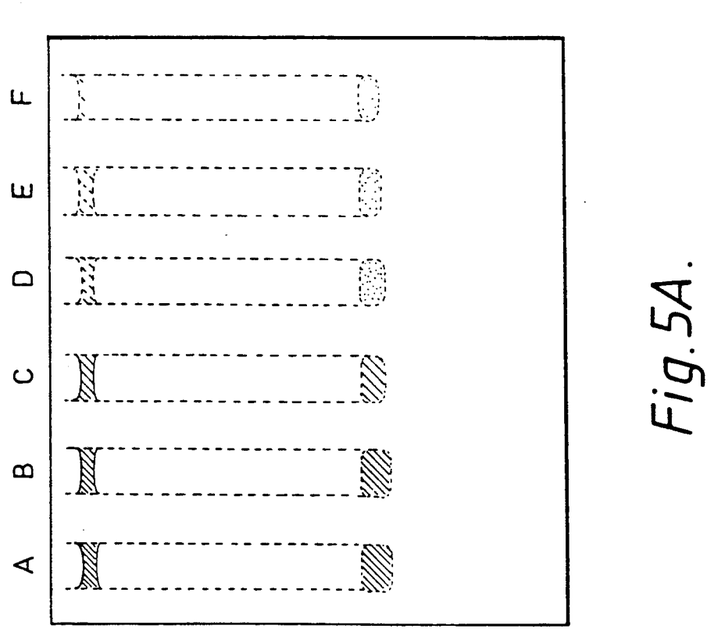
FIGS. 5a and 5b illustrate typical strained gels which are obtained using current reversal and smooth direct current, respectively, as a control
Figure 5B:
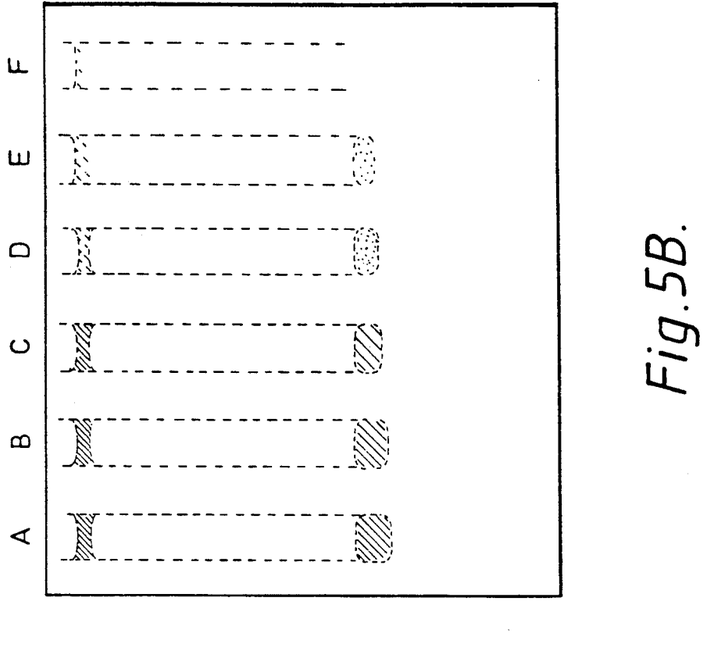

FIGS. 5a and 5b of the accompanying drawings, illustrate typical stained gels obtained using current reversal and smooth direct current as a control. FIG. 5a represents the result using current reversal. Traces A to F show the migration patterns of samples which contained initially at the origin (the top of each trace) 10, 5, 1, 0.5, 0.1 and 0.05 $\mu$g respectively. FIG. 5b represents the control using constant current, and the traces A to F have the same significance. In each instance in FIG. 5a, the final migrated zone is noticeably darker and more sharply defined than the corresponding migrated zone in the control (FIG. 5b), and indeed in migration pattern F, which contained the lowest concentration of starting material at the origin in the control trace, we have observed no migrated zone at all, indicating that all of the sample material had been distributed in the "tail" extending back to the origin. The corresponding trace F in FIG. 5a, shows a feint but clearly discernable migrated zone, demonstrating that the current reversal technique of the invention can significantly enhance the sensitivity of electrophoresis when dealing with extremely low quantities of sample material.

EXAMPLE 2

The example quoted above, indicated that a major reason for zone spreading is diffusion. Diffusion can most effectively be reduced by reducing the concentration gradient: that is to say, applying very small amounts of protein or nucleic acid. With very small amounts it is particularly important to avoid entrapment and trailing.

This example shows that the results obtained with current reversal for analysis of complex mixtures are superior to that obtained with ordinary DC.

Two gels were made, as for Example 1, but this time the buffer contained, in addition 0.1% (w/v) sodium dodecyl sulphate. Samples ranging from 1 to 10 $\mu$l of a porcine total muscle extract, containing approximately 10 mg/ml of protein were supplied, and then one gel run at 45 mamp for 165 minutes with current reversal while the other was run at 26 mamp for the same period, using the same variable power supply as in Example 1. Overall migration was closely similar in the two gels. After silver staining to detect protein it could clearly be seen that the zones were more compact when current reversal was used.

It was consistently observed that a clearer, sharper set of zones were obtained when current reversal was employed than when smoothed DC was used.

EXAMPLE 3

Figure 6:
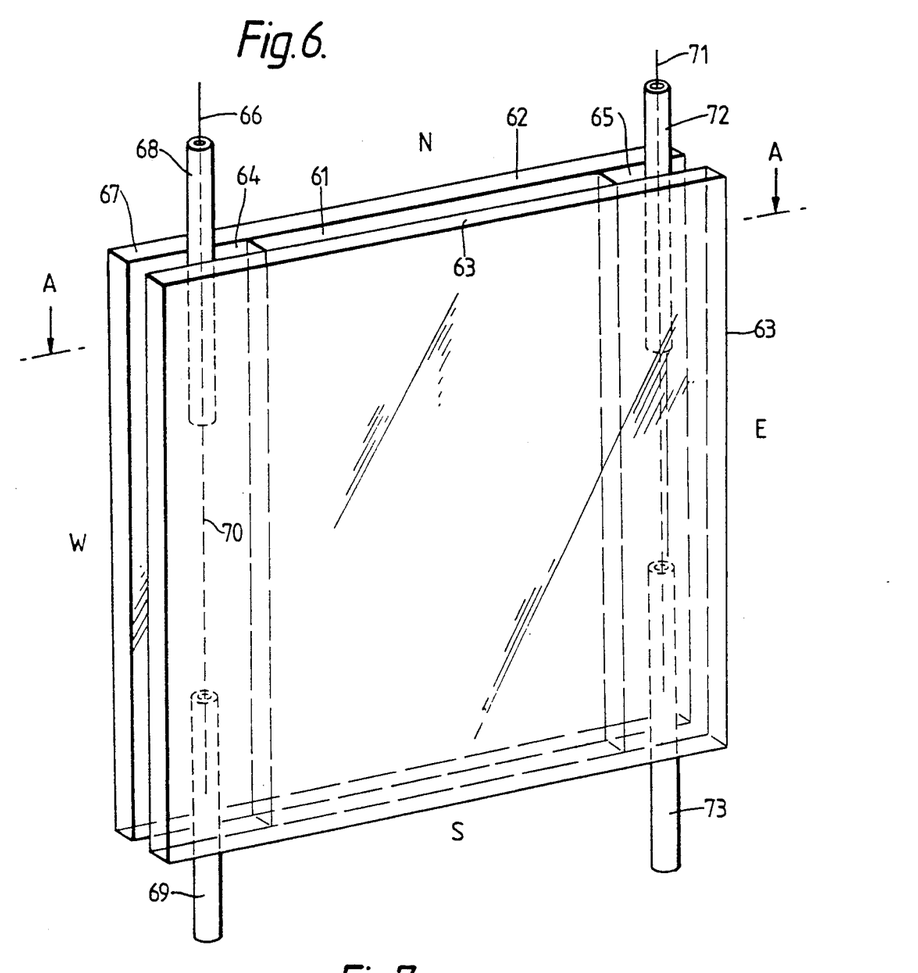
FIG. 6 illustrates an electrophoresis gel sandwiched between two glass plates with vertical gaps existing between the glass plates on each side of the electrophoresis gel.
Figure 7:
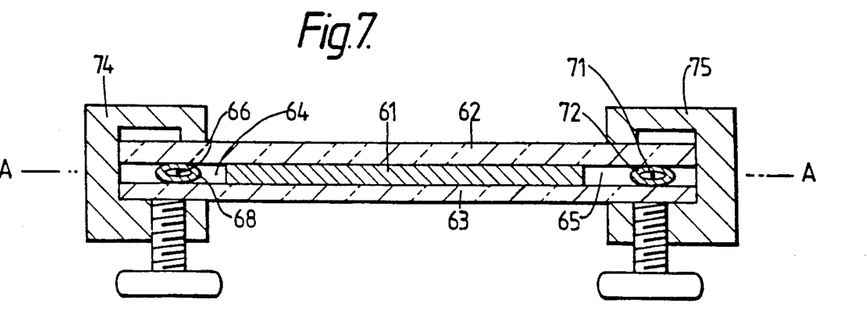
FIG. 7 illustrates an electrophoresis gel sandwiched between the glass plates cross-sectional view taken along line 8a of FIG. 6.

In this example current reversal was used in the separation of large fragments of DNA. The apparatus used included a modified vertical slab electrophoresis gel "cassette", which is illustrated in FIGS. 6 and 7 of the accompanying drawings. This comprised a standard glass plate cassette with a platinum wire electrode built into each side of the cassette.

Referring to FIG. 6, an electrophoresis gel 61 is sandwiched centrally between two glass plates 62 and 63. Both plates extend an equal distance beyond the gel on each side, and hence a vertical gap 64 and 65 exists between the plates adjacent their left-hand and right-hand sides respectively. A thin platinum wire electrode 66 runs into the gap 64 from the top 67 of the cassette. The wire is encased in upper and lower sleeves 68 and 69 formed from standard PTFE tubing of internal diameter 0.5 mm. The mid-portion 70 of the electrode is left bare. A similar electrode 71, encased in upper and lower PTFE sleeves 72 and 73, runs down into the gap 65 on the right hand side of the gel. Each electrode is held securely in place by compression of the sleeves when the glass plates are clamped together in the normal manner.

Referring to FIG. 7, which depicts a partial cross-section taken on the line AA shown in FIG. 6, the conventional screw clamps 74 and 75 holding the plates 62 and 63 together are seen. The positioning of the upper sleeves 68 and 72, containing the electrodes 66 and 71, relative to the gel 61 can be seen, with the intervening gaps 64 and 65 clearly visible. When this cassette is placed in a standard electrophoresis apparatus, this gap will be filled with buffer.

The platinum wires forming the electrodes extended upwards from the upper sleeves, passing through holes in the lid (not shown) of a standard electrophoresis cell, and were connected to an appropriate power unit. When fully assembled, the top and bottom of the glass plate cassette were immersed in the standard upper and lower buffer tanks which comprise part of the standard electrophoresis unit. Frosted glass plates were used to provide a secure hold on the gel cast between the plates. The gaps left between the side edges of the gel and the side electrodes ensured that any gassing of the electrodes during use did not cause disruption of the gel. This gap was easily provided by incorporating a removable spacer at each side of the gel during the casting process.

When fully assembled in an electrophoresis apparatus, the conventional electrodes provided a "N-S" potential, and the platinum wire side electrodes provided an "E-W" transverse potential.

The gel used was 1 mm thick, and cast from 1% (w/v) agarose in TRIS (0.09M) borate (0.09M) EDTA (1.5 mM) buffer adjusted to pH 8.5 using HCl. Samples were applied to pockets (not shown in the drawings) in the gel along the northern edge.

Figure 8:
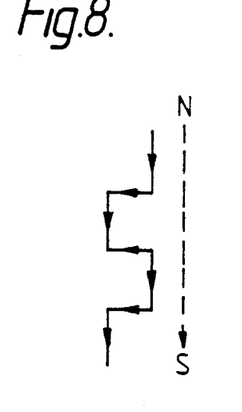
FIG. 8 illustrates the effect on the path of molecules when power was provided to an electrophoresis tank firstly N→S for 90 seconds when W→E for 60 seconds, N→S for 90 seconds, then E→W for 60 seconds. This switching cycle was then repeated indefinitely.

Power was provided to the electrophoresis tank such that 40 mamp and about 200 volts was applied, firstly N→S for 90 seconds, then W→E for 60 seconds, N→S for 90 seconds, then E→W for 60 seconds. This switching cycle was then repeated indefinitely. This was achieved using a switching circuit as depicted in FIG. 2 and described in principle earlier. A bipolar power supply obtained from a conventional electrophoresis power pack was switched using wet mercury relays controlled by individual commercially-available variable electronic timers having a range of 1-100 seconds. Short-circuiting effects due to the side electrodes were kept to a minimum because the platinum were forming the side electrodes was of thin enough (0.46 mm/SWG 26) to have a relatively high resistance compared to the buffer. The effect was that the molecules were constained to move in a boustrophedon manner, or 'as the ox ploughs', as depicted in FIG. 8. The advantage of this arrangement is that while the molecules were compelled to change direction by current reversal at intervals, the net result was still migration of a fairly linear manner from N→S in the gel.

By this method, some resolution of large fragments of DNA yeast chromosome fragments, T4 phage (166 kb) and lambda phage (40 kb), was obtained after about 6 hours of electrophoresis.

EXAMPLE 4

Figure 9:
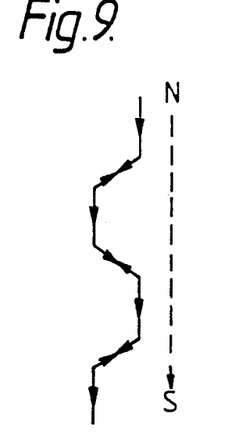
FIG. 9 illustrates the general effect on the path of molecules using a combination of variable power supplies. The basic switching sequence was 90 second N→S alone, 60 seconds N→S plus E→W, 90 seconds N→S alone, 60 seconds N→SA plus W→E. The N→S power source was permanently on, and not switched. The E→W and W→E power source was a high-frequency variable power unit with reversal for 1/16th of the time, 25 times a second. No power was taken from this source when the switch mechanism was in the N→S position.

In this example current reversal was achieved using a combination of the variable power supplies as used individually in Examples 1 and 2. The basic switching sequence was 90 seconds N→S along, 60 seconds N→S plus E→W, 90 seconds N→S alone, 60 seconds N→S plus W→E. The N→S power source was permanently on, and not switched. The E→W and W→E power source was the high-frequency variable power unit as used in Example 1 with reversal for 1/6th of the time, 25 times a second. No power was taken from this source when the switch mechanism was in the N→S position. In all directions, the applied potential was 200 volts, and the current was approximately 40 mamp. The general effect on the path of the molecules is shown in FIG. 9. Some resolution of yeast DNA fragments migrating more slowly than $T_4$ phage was obtained.

EXAMPLE 5

Figure 10:
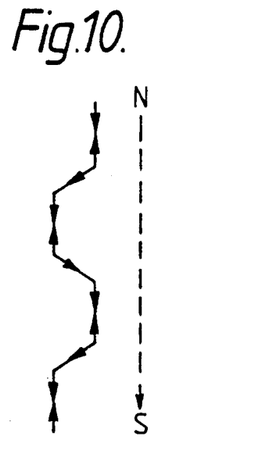
FIG. 10 illustrates the general effect of the path of molecules when an electrical current reversing 25 times a second, for 1/16th of the time, was permanently applied intermittently in the E→W and W→E directions.

In this example current reversal was used, with a switching sequence the same as that in Example 3. However, an electrical current reversing 25 times a second, for 1/6th of the time, was permanently applied in the N→S direction, while a DC source was applied intermittently in the E→W and W→E directions. Currents and voltages were as in Example 4. The general effect on the path of the molecules is shown in FIG. 10. The results obtained were similar to those in Example 4.

EXAMPLE 6

This example illustrates the use of current reversal at 200 volts and 40 mamp for 5 hours, without the use of transverse fields. This was conducted in conventional electrophoresis equipment, i.e. the side electrodes as described above (Example 3) were omitted. A power source was connected to the N→S pair of electrodes only and run continuously. It produced a field which was reversed for 1/6th of the time, 25 times a second. Large fragments of yeast DNA migrating more slowly than T4 phage, were seen in the gel after staining, although much of the DNA had barely entered the gel under these running conditions.

EXAMPLE 7

Example 6 was repeated but the switching unit as used in Example 3 was used to reverse the current less often. The DC power source was connected to the N→S pair of electrodes and then switched in such a way that it ran N→S for 10 seconds, and then S→N for 4 seconds, this cycle being repeated for 6 hours. The result was a net migration, and resolution, of large fragments of yeast DNA, as judged from their positions in the gel, where they migrated more slowly than $T_4$ phage and occupied positions all of the way back to the origin.

I claim:

1. The method of separating large macromolecules by electrophoresis which comprises introducing a sample of macromolecules at an origin location in a physically impeding gel-like medium and applying to said medium a forward electrical potential extending in a direction to move macromolecules in a predetermined direction away from the origin, and intermittently reversing the polarity of said electrical potential to establish reverse potential with the duration of the forward potential at least double the duration of the reverse potential wherein the forward potential is applied in the predetermined direction and a second electrical potential is applied with a component at right angles to the predetermined direction, and the polarity of the second electrical potential is intermittently reversed.

2. The method of separating large macromolecules by electrophoresis which comprises introducing a sample of macromolecules at an origin location in a physically impeding gel-like medium and applying to said medium a first electrical potential extending in a direction to move macromolecules in a predetermined direction away from the origin, and intermittently reversing the polarity of said first electrical potential to establish a second electrical potential which is the reverse of said first potential with the duration of said first potential at least double the duration of said second potential and applying a third electrical potential having a component which is at right angles to the direction of said first and second potentials and a fourth electrical potential which is the reverse of said third potential, the relative magnitudes and relative constancies or frequencies of the potentials being such that molecules experience a net influence in the predetermined direction.

* * * * *